United States Patent [19]
Tsuji et al.

[11] Patent Number: 6,017,743
[45] Date of Patent: Jan. 25, 2000

[54] SIAα 2,3, GALβ 1, 4GLC NACα 2,8-SIALYLTRANSFERASE

[75] Inventors: Shuichi Tsuji; Yukiko Yoshida; Naoya Kojima; Nobuyuki Kurosawa; Toshiro Hamamoto, all of Saitama, Japan

[73] Assignee: The Institute of Physical and Chemical Research, Saitama, Japan

[21] Appl. No.: 08/957,742

[22] Filed: Oct. 24, 1997

Related U.S. Application Data

[62] Division of application No. 08/626,994, Apr. 3, 1996, Pat. No. 5,798,244.

[30] Foreign Application Priority Data

Apr. 3, 1995 [JP] Japan ...................................... 7-77469

[51] Int. Cl.$^7$ .............................. C12N 15/54; C12N 9/10; C12N 15/63
[52] U.S. Cl. ..................... 435/193; 536/23.2; 435/320.1; 435/252.3
[58] Field of Search ........................ 536/23.2; 435/320.1, 435/252.3, 193

[56] References Cited

FOREIGN PATENT DOCUMENTS 9518217  7/1995  WIPO .

OTHER PUBLICATIONS

Varki, "Selectins and Other Mammalian Sialic Acid–binding Lectins", *Current Opinion in Cell Biology*, 4, pp. 257–266 (1992).

Hakomori, "Glycosphingolipids in Cellular Interaction, Differentiation, and Oncogenesis", *Ann. Rev. Biochem.*, 50, pp. 733–764 (1981).

Fishman et al., "Biosynthesis and Function of Gangliosides", *Science*, 194, pp. 906–915 (Nov. 26, 1976).

Broquet et al., "Glycoprotein Sialyltransferases in Eucaryotic Cells", *Int. J. Biochem.*, 23, pp. 385–389 (1991).

Weinstein et al., "Primary Structure of β–Galactoside α2,6–Sialyltransferase" *The Journal of Biological Chemistry*, 262, pp. 17735–17743 (Dec. 25, 1987).

Sadler et al., "Purification to Homogeneity of β– Galactoside α2→3 Sialyltransferase and Partial Purification of an α–N–Acetylgalactosaminide α2→6 Sialyltransferase from Porcine Submaxillary Glands", *The Journal of Biological Chemistry*, 254, pp. 4434–4443 (Jun. 10, 1979).

Weinstein et al., "Purification of Galβ1→4GlcNAc α2→6 Sialyltransferase and a Galβ1→3 (4) GlcNAc α2→3 Sialyltransferase to Homogeneity from Rat Liver", *The Journal of Biological Chemistry*, 257, pp. 13835–13844 Nov. 25, 1982).

Rearick et al., "Enzymatic Characterization of β–D–Galactoside α2→3 Sialyltransferase from Porcine Submaxillary Gland", The Journal of Biological Chemistry, 254, pp. 4444–4451 (Jun. 10, 1979).

Joziasse et al., "Purification and Enzymatic Characterization of CMP–sialic Acid: β–Galactosyl1→3–N–Acetylgalactosaminide α2→3–Sialyltransferase" *The Journal of Biological Chemistry* 260, pp. 4941–4951.

Grundmann et al., "Complete cDNA Sequence Encoding Human β–Galactoside α–2,6–Sialyltransferase", *Nucleic Acids Research*, 18, p. 667 (1990).

Bast et al., "The HB–6, CDw75, and CD76 Differentiation Antigens are Unique Cell–Surface Carbohydrate Determinants Generated by the β–Galactoside α2,6–Sialyltransferase", *The Journal of Cell Biology*, 116, pp. 423–435 (Jan. 1992).

Hamamoto et al., "Two Step Single Primer Mediated Polymerase Chain Reaction: Application to Cloning of Putative Mouse, β–Galactoside α2,6–Sialyltransferase cDNA", *Bioorganic & Medicinal Chemistry*, 1, pp. 141–145 (1993).

Gillespie et al., "Cloning and Expression of the Galβ, 3GalNAc α2,3–Sialyltransferase", *The Journal of Biological Chemistry*, 267, pp. 21004–21010 (Oct. 15, 1992).

Lee et al., "Molecular Cloning and Expression of Galβ1, 3GalNAcα2,3–Sialyltransferase from Mouse Brain", *Eur. J. Biochem.*, 216, pp. 377–385 (1993).

Wen et al., "Primary Structure of Galβ1,3(4)GlcNAc α2,3–Sialyltransferase Determined by Mass Spectrmetry Sequence Analysis and Molecular Cloning", *The Journal of Biological Chemistry*, 267, pp. 21011–21019 (Oct. 15, 1992).

Kurosawa et al., "Molecular Cloning and Expression of GalNac α2,6–Sialyltransferase ", *The Journal of Biological Chemistry*, 269, pp. 1402–1409 (Jan. 14, 1994).

Kurosawa et al., "Cloning and Expression of Galβ1, 3Gal-NAc–specific GalNAc α2,6–Sialyltransferase", *The Journal of Biological Chemistry*, 269, pp. 19048–19053 (Jul. 22, 1994).

Sasaki et al., "Expression Cloning of a Novel Galβ(1–3/1–4)GlcNAc α2,3–Sialyltransferase Using Lectin Resistance Selection", *The Journal of Biological Chemistry*, 268, pp. 22782–22787 (Oct. 25, 1993).

Lee et al., "Cloning and Expression of cDNA for a New Type of Galβ1, 3GalNAc α2,3–Sialyltransferase", *The Journal of Biological Chemistry*, 269, pp. 10028–10033 (Apr. 1, 1994).

*Primary Examiner*—Rebecca E. Prouty
*Attorney, Agent, or Firm*—Greenblum & Bernstein, P.L.C.

[57] ABSTRACT

The present invention provides a nucleotide sequence encoding Siaα2,3Galβ1,4GlcNAc α2,8-sialyltransferase and an enzymatically active fragment thereof. The present invention also provides a nucleotide sequence encoding an extracellularly releasable protein capable of catalyzing Siaα2,3Galβ1,4GlcNAc α2,8-sialyltransfer which comprises an enzymatically active fragment of the Siaα2, 3Galβ1,4GlcNAc α2,8-sialyltransferase together with a nucleotide sequence encoding at least one signal peptide. The present invention also provides recombinant vectors comprising nucleotide sequences encoding Siaα2,3Galβ1, 4GlcNAc α2,8-sialyltransferase. Processes for preparing extracellularly releasable polypeptide fragments of Siaα2, 3Galβ1,4GlcNAc α2,8-sialyltransferase are provided as well.

11 Claims, 4 Drawing Sheets

OTHER PUBLICATIONS

Troy, "Polysialylation: From Bacteria to Brains", *Glycobiology*, 2, pp. 5–23 (1992).

Edelman, "Cell Adhesion and the Molecular Processes of Morphogenesis", *Ann. Rev. Biochem.*, 54, pp. 135–169 (1985).

Cunningham et al., "Neural Cell Adhesion Molecule: Structure, Immunogloblin–Like Domains, Cell Surface Modulation, and Alternative RNA Splicing", *Science*, 236, pp. 799–806 (May 15, 1987).

Rutishauser et al, "The Neural Cell Adhesion Molecule (NCAM) as a Regulator of Cell–Cell Interactions", *Science*, 240, pp. 53–57 (Apr. 1, 1988).

Zuber et al., "Polysialic Acid is Associated with Sodium Channels and the Neural Cell Adhesion Molecule N–CAM in Adult Rat Brain", *The Journal of Biological Chemistry*, 267, pp. 9965–9971 (May 15, 1992).

Sasaki et al., "Expression Cloning of a $G_{M3}$–specific α–2, 8–Sialyltransferase ($G_{O3}$ Synthase)", *The Journal of Biological Chemistry*, 269, pp. 15950–15956 (Jun. 3, 1994).

Kojima et al., "Enzymatic Activity of a Developmentally Regulated Member of the Sialyltransferase Family (STX): Evidence for α2,8–Sialyltransferase Activity Toward N–linked Oligosaccharides", *FEBS Letters*, 360, pp. 1–4 (1995).

Kojima et al., "A Developmentally Regulated Member of the Sialyltransferase Family (ST8Sia II, STX) is a Polysialic Acid Synthase", *FEBS Letters*, 373, pp. 119–122 (1995).

Edelman, *Science*, vol. 219, pp. 450–457 (1983).

Finne, *The Journal of Biological Chemistry*, vol. 257, pp. 11966–11970 (1982).

Haraguchi et al., *Proceedings of the National Academy of Sciences USA*, vol. 91, pp. 10455–10459 (1994).

Hoffman et al., *The Journal of Biological Chemistry*, vol. 257, pp. 7720–7729 (1982).

Jobling and Gehrke, *Nature*, vol. 325, pp. 622–625 (1987).

Kyte and Doolittle, *Journal of Molecular Biology*, vol. 157, pp. 105–132 (1982).

Livingston et al., *Glycobiology*, vol. 1, pp. 39–44 (1990).

Livingston and Paulson, *The Journal of Biological Chemistry*, vol. 268, pp. 11504–11507 (1993).

McCoy et al., *The Journal of Biological Chemistry*, vol. 260, pp. 12695–12699 (1985).

Nara et al. *Proceedings of the National Academy of SciencesUSA*, vol. 91, pp. 7952–7956 (1994).

Paulson and Colley, *The Journal of Biological Chemistry*, vol. 264, pp. 17615–17618 (1989).

Yoshida et al., *The Journal of Biological Chemistry*, vol. 270, pp. 14628–14633 (Jun. 16, 1995).

Sasaki et al., *J. Biol. Chem.* 269(20): 14730–14737 (1994).

Kitagawa et al., *J. Biol. Chem.* 269(27): 17872–17878 (1994).

Kurosawa et al., *European J. Biochem.* 219 (1–2): 375–381 (1994).

```
ST8Sia-II(STX)      MQ---LQFRSWMLAALTLLVVFLIFADISEIE---EEIGNSGGRGTIRSA
ST8Sia-III          MRNCKMARVASVLGLVMLSVALLILSLISYVSLKKENIFTTPKYASPGAP
ST8Sia-I            MSPCGRALHTSRGAMAMLARKF------------------PRTRLPVG
(GD3 synthase)

ST8Sia-II(STX)      VNSLHSKSNRAEVVINGSSPPAVADRSNESLKHNIQPASSKWRHNQTLSL
ST8Sia-III          RMYMFHAGFRSQFALKFLDQSFVP--ITNSLTHELQEKPSKWTFNRTAFL
ST8Sia-I            ASALCVVVLCWLYIFPVYRPP-----NEKEIVQGVLAQSTAWRTNQTSAS
(GD3 synthase)

ST8Sia-II(STX)      RIRKQILKFLDAEKDISVLKGTLKPGDIIHYIFDRDS-TMNVSQNLYELL
ST8Sia-III          HQRQEILQHVDVIKNFSLTKSSVRIGQLMHYDYSSHKYVFSISNNFRSLL
ST8Sia-I            LFRRQMEDCCDPAHLFAMTKMNSPMGKSLWYD-GELLYSFTIDNSTYSLF
(GD3 synthase)

ST8Sia-II(STX)      PRTSPLKNKHFQTCAIVGNSGVLLNSGCGQEIDTHSFVIRCNRAPVQ-EY
ST8Sia-III          PDVSPIMNKRYNVCAVVGNSGILTGSQCGQEIDKSDFVSRCNFAPTE-AF
ST8Sia-I            PQATPF-QLPLKKCAVVGNGGILKMSGCGRQIDEANFVMRCNLPPLSSEY
(GD3 synthase)

ST8Sia-II(STX)      ARDVGLKTDLVTMNPSVIQRAFEDLVNATWREKLLQRLHGLNGSILWIPA
ST8Sia-III          HKDVGRKTNLTIFNPSILEKYYNNLLTIQDRNNFFLSLKKLDGAILWIPA
ST8Sia-I            TRDVGSKTQLVTANPSIIRQRFENLLWS--RKKFVDNMKIYNHSYIYMPA
(GD3 synthase)

ST8Sia-II(STX)      FMARGGKERVEWVNALILKH--HVNVRTAYPSLRLLHAVRGYWLTNKVHI
ST8Sia III          FFFHTSATVTRTLVDFFVEHRGQLKVQLAWPG-NIMQHVNRYWKNKHLSP
ST8Sia-I            FSMKTGTEPSLRVY-YTLKDVGANQTVL-FANPNFLRNIGKFWKSRGIHA
(GD3 synthase)

ST8Sia-II(STX)      KRPTTGLLMYTLATRFCNQTYLYGFWPFPLDQN-QNPVKYHYYDSLKYGY
ST8Sia-III          KRLSTGILMYTLASAICEEIHLYGFWPFGFDPNTREDLPYHYYDKKGTKF
ST8Sia-I            KRLSTGLFLVSAALGLCEEVSIYGSWPFSVNMQG-DPISHHYYDNV-LPF
(GD3 synthase)

ST8Sia-II(STX)      TSQ-ASPHTMPLEFKALKSLHEQGALKLTVGQCDGAT-----   375
ST8Sia-III          TTKWQESHQLPAEFQLLYRMHGEGLTKLTLSHC---A-----   380
ST8Sia-I            TG----YHAMPEEFLQLWYLHRIGALRMQLDPCEAPSPQPTS   355
(GD3 synthase)
```

SIAα 2,3, GALβ 1, 4GLC NACα 2,8-SIALYLTRANSFERASE

This application is a division, of application Ser. No. 08/626,994, filed Apr. 3, 1996, now U.S. Pat. No. 5,798,244.

FIELD OF THE INVENTION

The present invention relates to an enzyme catalyzing syntheses of saccharide chains and to DNAs encoding said enzyme More specifically, the present invention relates to a novel α 2,8-sialyltransferase (ST8SiaIII) having activities toward Sia α 2,3Gal β 1,4GlcNAc sequences of N-linked oligosaccharides and glicolipids, and to DNAs encoding the enzyme. The enzyme is useful as a medicament having pharmacological activities such as prevention of cancerous metastasis, maturation of sperm, inhibition of inflammatory reactions, and re-activation of nervous tissues. The enzyme is also useful as an agent for introducing oligosialic acids such as di-, tri-, or tetra-sialic acid to glyco-proteins and glycolipids for increasing physiological activities.

BACKGROUND OF THE INVENTION

Sialic acids are responsible for important physiological actions such as intercellular transmissions, cytoplasmic interactions, and cellular adhesions. Existences of wide variety of different cell-surface sialic acids are known, and they are regulated in processes of generations, differenciations, and transformations of oncogenes. Sialic acids are ubiquitous in the oligosaccharide side chains of glycoconjugates of a wide variety of animals (Varki, A., Curr. Opin. Cell. Biol. 4, pp.257–266, 1992).

Sialic acids exist at the end of hydrocarbon groups of glycoproteins and glycolipids. Sialic acids are enzymatically introduced to these positions from CMP-Sia during post-translation processes. For example, three sequential types, i.e., Siaα 2,6Gal, Siaα 2,3Gal, and Siaα 2,6GalNAc, commonly exist in glycoproteins (Hakomori, S., Ann. Rev. Biochem., 50, 733–764, 1981), and two sequential types, i.e. Siaα 2,3Gal and Siaα 2,8Sia, are frequently observed in ganglyosides (Fishman, P., and Brady, R. O., Science, 194, 906–915, 1976).

Enzymes responsible for the above-mentioned enzymatic introductions of sialic acids (i.e. sialyltransfers) are glycosyltransferases that are reffered to as sialyltransferases. It has been found that at least twelve different sialyltransferases are required for preparations of all types of the sialyloligosaccha ride structures so far known (Broquet, P. et al., Int. J. Biochem., 23, 385–389, 1991; and Weinstein, J. et al., J. Biol. Chem., 262, 17735–17743, 1987). Among then, five sialyltransferases were purified and each of the purified enzymes was found to exhibit high specificities to respective acceptor substrates (Sadler, J. et al., J. Bio. Chem., 254, 4434–4443, 1979; Weinstein, J. et al., J. Biol. Chem., 257, 13835–13844, 1982; Rearick, J. et al., J. Biol. Chem., 254, 4444–4451, 1979; and Joziasse, D. H. et al., J. Biol. Chem., 260, 4941–4951, 1985).

With regard to cDNAs encoding the aforementioned sialyltransferases, cDNAs encoding Galβ 1,4GlcNAcα 2,6-sialyltransferases (Galβ 4GlcNAc-α 6ST) were cloned from various tissues such as liver (Weinstein, J. et al., J. Biol. Chem., 262, 17735–17743, 1987; Grundmann U. et al., Nucleic Acids Res. 18, 667, 1990; Bast, B. et al., J. Cell. Biol., 116, 423–435, 1992; and Hamamoto, T. et al., Bioorg. and Medic. Chem., 1, 141–145, 1993). In addition, cDNAs encoding Galβ 1,3GalNAcα 2,3-sialyltransferases (Galβ 3GalNAc-α 3ST: Gillespie, W. et al., J. Biol. Chem., 267, 21004–21010, 1992; and Lee, Y. et al., Eur. J. Biochem, 216, 377–385, 1993), and a cDNA encoding Galβ 1,3(4) GlcNAcα 2,3-sialyltransferase (Galβ 3(4)GlcNAc-α 3ST: Wen, D. X et al., J. Biol. Chem., 267, 21011–21019, 1992) were also cloned.

Furthermore, cDNAs encoding two different types of GalNAcα 2,6-sialyltransferases (EC 2.4.99.3; GalNAc-α 6ST) were cloned by the inventors of the present invention, and their soluble proteins were prepared (Kurosawa, N. et al., J. Biol. Chem., 269, pp.1402–1409, 1994; and Kurosawa, N. et al., J. Biol. Chem., 269, pp.19048–19053, 1994). Some other publications also relate to clonings of cDNAs encoding sialyltransferases (e.g. Sasaki, K. et al., J. Biol. Chem., 268, 22782–22787, 1993; and Lee, Y.-C., J. Biol. Chem., 269, 10028–10033, 1994).

Siaα 2,8Sia-sequences are widely observed in various gangliosides such as GT1a, GD3, and b- and c-series of gangliosides, and are more specifically found in mammal glycoproteins (Troy, F. A., Glycobiology 2, pp.5–23, 1992). It has been reported that Siaα 2,8Sia-sequences are associated with only two proteins, i.e. the neutral cell adhesion molecule (N-CAM: Edelman, G. M., Annu. Rev. Biochem. 54, pp.135–169, 1985; Cunningham, B. A. et al., Science, 236, pp.799–806, 1987; and Rutishauser, U. et al., Science, 240, pp.53–57, 1988) and the α subunit of the voltage-gated sodium channels in rat brain (Zuber, C., J. Biol. Chem., 267, pp.9965–9971, 1992).

Recently, the inventors of the present invention cloned an α 2,8-sialyltransferase, i.e. GD3-synthase (ST8SiaI: Sasaki, K. et al., J. Biol. Chem., 269, pp.15950–15956, 1994), and reported that a developmentally regulated sialyltransferase (STX, ST8SiaII) have N-glycan α2,8-sialyltransfer activity and polysialic acid synthesizing activity (Kojima, N. et al., FEBS Lett., 360, pp.1–4, 1995, and FEBS Lett., 373, pp.119–122, 1995). However, only two cDNAs encoding α 2,8-sialyltransferase have been cloned so far, and the substrate specificities of these cloned α 2,8-sialyltransferases do not give a full explanation as to how all of the Known Siaα 2,8-Sia sequences in mammal glycolipids and glycoproteins are synthesized.

SUMMARY OF THE INVENTION

An object of the present invention is to provide a novel type of α 2,8-sialyltransferase. Other objects of the present invention are to provide the amino-acid sequence of the α 2,8-sialyltransferase and a cDNA encoding the same. Further object of the present invention is to provide a extracellularly releasable protein comprising an enzymatically active domein of the α 2,3-sialyltransferase, and a method for mass production of such protein.

The inventors of the present invention conducted various studies to achieve the foregoing objects, and as a result, they cloned the cDNA encoding the Siaα 2,3Galβ 1,4GlcNAc α 2,8-sialyltransferase from the mouse brain. The present invention was achieved on the basis of the above findings.

The present invention thus provides novel Siaα 2,3Galβ 1,4GlcNAc α 2,8-sialyltransferase, and as a preferred embodiment thereof, Siaα 2,3Galβ 1,4GlcNAc α 2,8-sialyltransferase O3 characterized by the amino-acid sequence of SEQ. ID. No.1 disclosed in the sequence listing.

According to another aspect of the present invention, nucleic acid sequences encoding said Siaα 2,3Galβ 1,4GlcNAc α 2,8-sialyltransferase are provided. As a preferred embodinent of the present invention, there is provided the Siaα 2,3Galβ 1,4GlcNAc α 2,8-sialyltransferase gene characterized by from nucleotide No. 123 to 1214 of the nucleic acid sequence of SEQ. ID. NO. 2 disclosed in the sequence listing.

A recombinant vector containing said Siaα 2,3Galβ 1,4GlcNAc α 2,8-sialyltransferase gene, and as a preferred embodiment, plasmide λ CR03 are provided. A microorganism transformed by at least one of said vectors is also provided.

According to further aspect of the present invention, a enzymatically active domein of the Siaα 2,3Galβ 1,4GlcNAc α 2,8-sialyltransferase is provided. As a preferred embodiment, the peptide sequence characterized by from amino acid No.26 to No.364 of SEQ. ID. No.1 is provided. Also provided is a polypeptide comprising said enzymatically active domein of the Siaα 2,3Galβ 1,4GlcNAc α 2,8-sialyltransferase.

According to yet another aspect of the present invention, there is provided an extracellularly releasable protein capable of catalyzing a Siaα 2,3Galβ 1,4GlcNAc α 2,8-sialyltransfer which comprises the polypeptide comprising the enzymatically active domein of the Siaα 2,3Galβ 1,4GlcNAc α 2,8-sialyltransferase together with at least one signal peptide. As a preferred embodiment thereof, a soluble protein characterized by the amino acid sequence of SEQ. ID. No.3 is provided.

There are also privided a gene encoding said protein, and as a preferred embodiment thereof, the gene characterized by the nucleic acid sequence of from nucleotide No. 14 to 1030 of SEQ. ID. NO. 4. Also provided are a recombinant vector containing said gene encoding the protein, a microorganism transformed by at least one of the recombinant vectors, and a method for preparing the extracellularly releasable protein comprising the steps of cultivating the transformant and recovering said protein from the culture.

BRIEF DESCRIPTION OF THE DRAWINGS

FIG. 1 depicts the nucleic acid sequence (SEQ. ID. No.2) encoding Siaα 2,3Galβ 1,4GlcNAc α 2,8-sialyltransferase O3 (mouse ST8Sia-III) as a preferred example of the Siaα 2,3Galβ 1,4GlcNAc α 2,8-sialyltransferases of the present invention, and deduced amino acid sequence thereof. In the figure, the double underlined amino acids correspond to a putative transmembrane domain, and the asterisks indicate potential N-glycosylation sites (Asn-X-Ser/Thr). Sialyl motifs L and S are boxed by solid and dashed lines, respectively, and the positions of the PCR primers are indicated by arrows. The amino acids are shown by the one-letter symbol.

FIG. 2 shows the amino acid sequence of the α 2,8-sialyltransferase O3 of the present invention as compared to those of mouse ST8SiaI and mouse ST8SiaII. In the figure, amino acids are indicated by one letter symbol and ST8Sia-III represents the Sia α 2,3Galβ 1,4GlcNAc α 2,8-sialyltransferase O3 of the present invention. The amino acids shared with ST8Sia-III and other sialyltransferases are shaded and sialyl motifs L and S are underlined.

DETAILED DESCRIPTION

A. Preferred Embodiments

Figure 3:
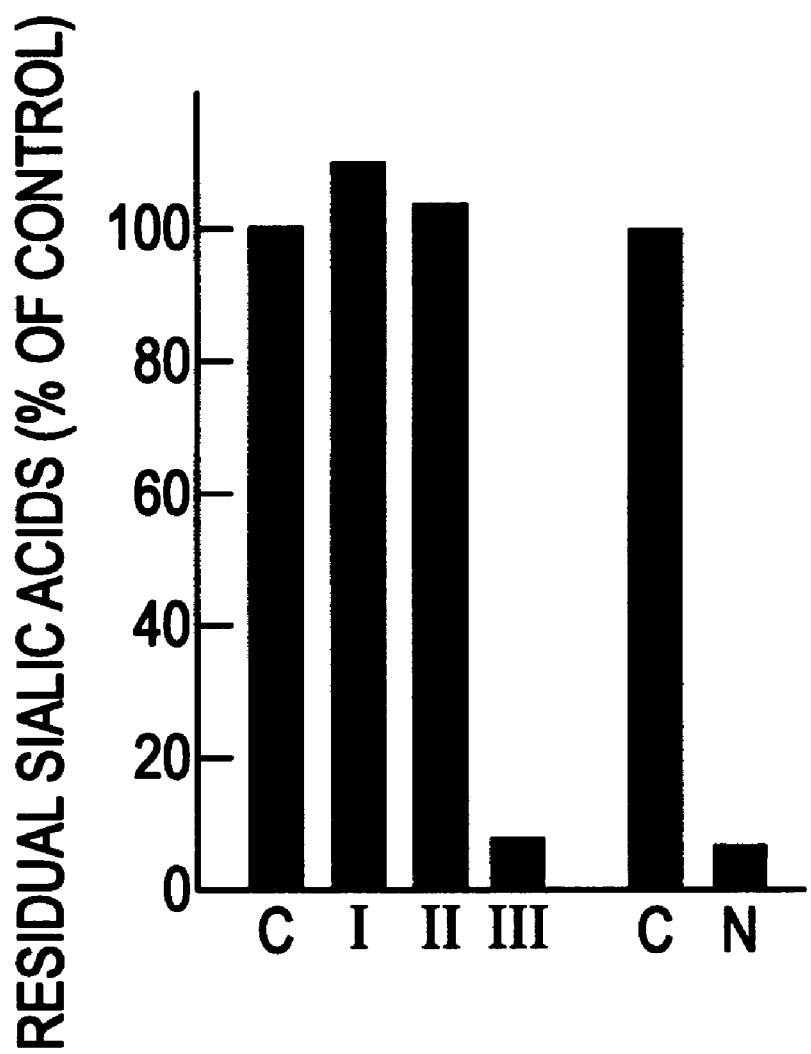
FIG. 3 shows the results of linkage analysis of sialic acids incorporated by the α 2,8-sialyltransferase of the present invention. In the figure, C, I, II, III, and N represent treatment with no enzyme, NANase I, NANase II, NANase III, and N-glycanase, respectively.

As the most preferred example of the Siaα 2,3Galβ 1,4GlcNAc α 2,8-sialyltransferase of the present invention, Siaα 2,3Galβ 1,4GlcNAc α 2,8-sialyltransferase O3 (SEQ. ID. No.1) is provided. The following descriptions detail the preparation and enzymatic characterizations of the α 2,8-sialyltransferase O3. However, the Siaα 2,3Galβ 1,4GlcNAC α 2,8-sialyltransferase of the present invention is not limited to the α 2,8-sialyltransferase O3, and thus the term "Siaα 2,3Galβ 1,4GlcNAc α 2,8-sialyltransferase" as used herein means the polypeptide having the amino acid sequence set forth as SEQ. ID. No.1 as well as amino acid sequence variants thereof that are enzymatically active in Siaα 2,3Galβ 1,4GlcNAc α 2,8-sialyltransfer. Examples of means for preparing such amino acid variants include, for example, substitution, insertion, and deletion of one or more amino acids.

The term "genes encoding the Siaα 2,3Galβ 1,4GlcNAc α 2,8-sialyltransferase" as herein means the nucleic acid sequence as set forth in SEQ. ID. No.2 and nucleic acid variants thereof, as well as DNAs encoding the amino-acid sequence of the above defined Sia α 2,3Galβ 1,4GlcNAc α 2,8-sialyltransferase including α2,8-sialyltransferase O3 and variants thereof. Examples of means for preparing such nucleic acid variants include, for example, substitution, insertion, and deletion of one or more nucleic acids. A detailed procedure for the cloning and expression of the gene encoding the Sia α 2,3Galβ 1,4GlcNAc α 2,8-sialyltransferase O3 (SEQ. ID. No.2), as a particularly preferred embodiment, will be set forth in the following Example. However, the descriptions are offerd by way of illustration only and are not intended to limit the present invention in any manner. It can readily be understood by an ordinary artisan that desired DNAs encoding α 2,8-sialyltransferase of the present inveniton can be separated according to the experimental procedures disclosed in Example, together with appropriate modifications or alterations, if necessary.

Additionally, polypeptides comprising one or more enzymatically active domeins derived from the Siaα 2,3Galβ 1,4GlcNAc α 2,8-sialyltransferase of the present invention fall within the scope of the present invention. The term "enzymatically active domein" as used herein means a polypeptide sequence which is derived from the above-defined Siaα 2,3Galβ 1,GlcNAc α 2,8-sialyltransferase including the α 2,8-sialyltra-sferase O3 and variants thereof and is enzymatically active in Siaα 2,3Galβ 1,4GlcNAc α 2,8-sialyltransfer. An example of such enzymatically active domeins is a part of the full polypeptide sequence of the α 2,8-sialyltransferase O3 (SEQ. ID. No.1) which is characterized by the sequence of from amino acid No. 26 to 364 of SEQ. ID. No.1. Examples of the DNA encoding the enzymatically active domein include, for examle, the nucleic acid sequence encoding the polypeptide sequence characterized by the sequence of from amino acid No. 26 to 364 in SEQ. ID. No.1, and a preferred example thereof includes the nucleotide sequence characterized by from nucleic acid No. 198 to 1214 of SEQ. ID. NO. 2.

It has been found that Siaα 2,3Galβ 1,4GlcNAc α 2,8-sialyltransferase O3 stays inside host cells after its expression and remain unreleased extracellularly. In addition, the enzyme expressions may be decreased when endoplasmic concentration of the enzyme is above a certain threshold level. In order to efficiently utilize the Siaα 2,3Galβ

1,4GlcNAc α 2,8-sialyltransfer activity of the sialyltransferase of the present invention, soluble proteins can be prepared that retain the sialyltransfer enzymatic activity and are capable of being released from host cells after expression. An example of such soluble proteins includes, for example, an extracellularly releasable protein capable of catalyzing Siaα 2,3Galβ 1,4GlcNAc α 2,8-sialyltransfer which comprises the enzymatically active domein derived from the Siaα 2,3Galβ 1,4GlcNAc α 2,8-sialyltransferase of the present invention together with one or more signal peptides. The fused protein (SEQ. ID. No.3) comprising protein A and the enzymatically active domein of α 2,8-sialyltransferase O3 is a particularly preferred example of the soluble protein.

The sialyltransferases so far cloned have domein structures similar to other glycosyltransferases, i.e. a short endoplasmic N-terminal tail; a hydrophobic signal anchor domein; a stem region having a protease sensitivity; and a large active domein at COOH-terminal (Paulson, J. C. and Colley, K. J., J. Biol. Chem., 264, 17615–17618, 1989). For the determination of a transmembrane region of the Siaα 2,3Galβ 1,4GlcNAc α 2,8-sialyltransferase of the present invention, a hydrophobic index profile may be prepared and used according to the method of Kyte and Doolittle (Kyte, J. and Doolittle, R. F., J. Mol. Biol., 157, 105–132, 1982). For deducing the enzymatically active domeins, recombinant plasmides introduced with various fragments can be prepared and used. Detailed procedures are described in the specification of PCT/JP94/2182 in reference to the determination of the transmembrane region and the deduction of the enzymatically active domeins. However, applicable procedures are not limited to those disclosed procedures.

For the preparation of the extracellularly releasable protein, an immunoglobulin signal peptide sequence may be preferably used as the signal peptide, and the enzymatically active sequence derived from the α 2,8-sialyltransferase of the present invention may preferably be subjected to an inflame fusion with said signal peptide. For example, the method of Jobling may be applied to the inflame fusion (Jobling, S. A. and Gehrke, L., Nature(Lond.), 325, 622–625, 1987). Example set forth below details the preparation of the fused protein using protein A. However, types of the signal peptides and methods for preparing the soluble proteins are not limited to the disclosed procedures. It can readily understood by an ordinary artisan that the enzymatically active domein can be suitably chosen from the Sia α 2,3Galβ 1,4GlcNAc α 2,8-sialyltransferase of the present invention, and that the extracellularly releasable proteins can easily be prepared by combining the active domein with one or more appropriate signal peptides according to known methods.

The enzyme of the present invention is characterized as a α 2,8-sialyltransferase specific to Siaα 2,3Galβ 1,4GlcNAc sequence of N-linked oligosaccharides. The sialyltransferase of the present invention is thus useful as enzymatic agents for introducing a polysialic acid or an oligosialic acid such as di-, tri-, or tetra-sialic acid to proteins. The sialyltransferase of the present invention is also useful as medicaments for therapeutic treatments for hereditary diseases lacking enzymes for the biosynthesis of specified sugar chains. In addition, the sialyltransferase of the present invention is useful as medicaments for inhibition and prevention of cancerous metastasis or inflammatory reactions, or regeneration and re-activation of nervous tissues.

B. Examples

The gene encoding GD3 synthase (ST8Sia I) was cloned from human (Sasaki, K. et al., J. Biol. Chem. 269, pp.15950–15956, 1994; Nara, K. et al., Proc. Natl. Acad. Sci. U.S.A. 91, pp.952–7956, 1994; Haraguchi, M. et al., Proc. Natl. Acad. Sci. U.S.A. 91, pp.10455–10459, 1994) and mounse. Recently, the inventors of the present invention identified the enzymatic activity of mouse STX (ST8Sia II) as that of an N-glycan α2,8-sialyltransferase and polysialic acid synthase (Kojima, N. et al., FEBS Lett., 360, pp.1–4, 1995, and FEBS Lett., 373, pp.119–122, 1995). To obtain the α2,8-sialyltransferase of the present invention that is characterized by properties distinguishable from the known α 2,8-sialyltransferases, the inventors of the present invention conducted PCR cloning experiments using two degenerate oligonucleotide primers based on two highly conserved regions, sialyl motifs L and S, of human ST8Sia I (Sasaki, K. et al., J. Biol. Chem. 269, pp.15950–15956, 1994) and rat ST8Sia II (Livingston, B. D. et al., J. Biol. Chem., 268, pp.11504–11507, 1993).

PCR was performed using degenerate primers (5'-primer OP-L, T(G/A)(A/C)AGA(A/C)(A/T)TG(C/T)GC(G/C)(G/A)T(G/C)GTGGG(A/C)AA; 3'-primer OP-S, CA(C/A)(A/T)G(A/G)GAAGGGCCAGAAGCCATA) deduced from conserved regions in STX (rat brain: Livingston, B. D. et al., J. Biol. Chem., 268, pp.11504–11507, 1993) and GD3 synthase (human melanoma cells: Sasaki, K. et al., J. Biol. Chem. 269, pp.15950–15956, 1994). Total RNA from 3-day-old mouse brain was used as a template to synthesize cDNA. The cycling parameters were 94° C. for 40 sec, 37° C. for 40 sec, and 72° C. for 1 min for the first 5 cycles, followed by 94° C. for 40 sec, 55° C. for 40 sec, and 72° C. for 1 min for 30 cycles.

The 0.5-Kb PCR products were blunt-ended, kinased, and then subcloned into the SmaI site of pUC119. The subclones were characterized by sequencing. Approximately $10^6$ plaques of a 3-day-old mouse brain cDNA library (Lee, Y.-C. et al., J. Biol. Chem., 269, pp.10028–10033, 1994) were screened with the 0.5-kb-PCR fragments. Standard molecular cloning techniques, according to Maniatis et al., were used (Sambrook, J., Fritsch, E. F., and Maniatis, T., Molecular Cloning: a Laboratory Manual, 2nd edition, Cold Spring Harbor Laboratory, Cold Spring Harbor, N.Y., 1989).

Figure 1:
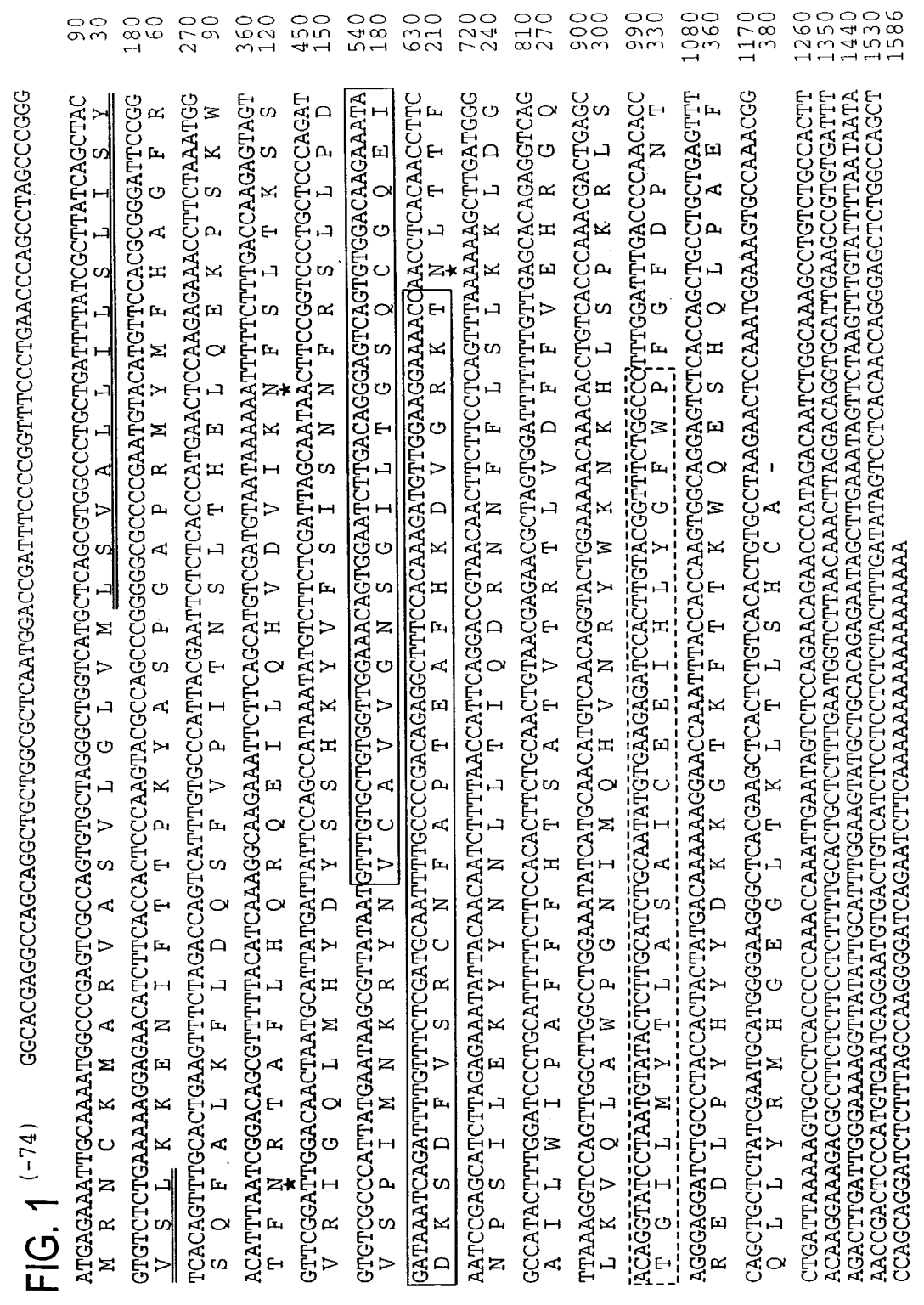

Among several clones, one clone, pCRO3, encoded a peptide exhibiting 35.6% and 41.9% identity to the 160-amino acid region of mouse ST8Sia I and mouse ST8Sia II, respectively. To isolate the complete coding sequence of the gene containing the 0.5-kb fragment, the mouse brain cDNA library was screened using the pCRO3 probe. Sequence analysis of the largest clone (1.7 kb; λ CRO3) revealed a continuous 380-amino acid open reading frame, including 74-bp of 5' and 465-bp of a 3' non-coding region. FIG. 1 and SEQ. ID. No.2 depict the aforementioned DNA sequence of λ CRO3, as a preferred example of the DNAs encoding Siaα 2,3Galβ 1,4GlcNAc α 2,8-sialyltransferase of the present invention, and the amino acid sequence of Siaα 2,3Galβ 1,4GlcNAcα 2,8-sialyltransferase (mouse ST8Sia-III) encoded by the nucleotide sequence.

In FIG. 1, the nucleotide and amino acid sequences are numbered from the presumed start codon and initiation methionine, respectively. The double underlined amino acids correspond to a putative transmembrane domein. The asterisks indicate potential N-glycosylation sites (Asn-X-Ser/Thr). Sialyl motifs L and S are boxed by solid and dashed lines, respectively. The positions of the PCR primers are indicated by arrows. The predicted amino acid sequence encoding a protein with a type II transmembrane domein, as found for so far cloned sialyltransferases, consisted of a $NH_2$-terminal cytoplasmic tail, a transmembrane domain, a proline-rich stem region, and a large COOH-terminal active domein.

Comparison of the amino acid sequence of the sialyltransferase of the present invention with other amino acid sequences in DNA and protein data banks did not reveal any similarity except with so far cloned sialyltransferases. On the other hand, some similarities were observed between the sialyltransferase of the present invention and other so far cloned sialyltransferases. The deduced amino acid sequence shows 27.6% and 34.4% identity to those of mouse ST8Sia I and mouse ST8Sia II, respectively (FIG. 2, wherein ST8Sia-III represents Siaα 2,3Galβ 1,4GlcNAcα 2,8-sialyltransferase O3 of the present invention.). However, there is no significant similarity (10–15%) except for two stretches of sialyl motif L (45 residues: 165–205) and S (23 residues: 301–323) amino acids located in their active domeins. Sialyl motif L shows 64–49% sequence identity, whereas sialyl motif S exhibits 61–22% identity to those of so far cloned sialyltransferases.

To facilitate functional analysis of the sialyltransferase of the present invention, expression plasmid pcDSA-O3 was constructed and transfected into COS-7 cells, and the protein A fused-protein containing an active domein of the sialyltransferase of the present invention (i.e. a soluble enzyme; hereinafter referred to as the fused protein of the present invention) was adsorbed to IgG-Sepharose in the medium and used as the enzyme source. The amino acid sequence of the fused protein and the gene encoding the fused protein are shown as SEQ. ID. No.3 and 4, respectively.

A truncated form of the sialyltransferase of the present invention (ST8Sia-III), lacking the first 39 amino acids of the open reading frame, was prepared by PCR amplification with 5'- and 3'-primers containing a XhoI site, respectively (5'-CATCTTCTCGAGTCCC AAGTACGCCAGCCCG-3' and 5'-TTCCAT CTCGAGTTCTTAGGCACAGTGTGACAG-3'). The amplified and digested 1028-bp XhoI fragment was inserted into the XhoI site of a pcDSA vector (Kojima, N. et al., FEBS Lett., 360, pp.1–4, 1995).

The single insertion in the correct orientation was finally analyzed by restriction enzyme treatment and DNA sequencing. The resulting plasmid was designated as pcDSA-O3, which consisted of the IgM signal peptide sequence, a protein A IgG binding domain, and a truncated form of ST8Sia-III. COS-7 cells were transiently transfected with 10 μg of pcDSA-ST8Sia-III using the DEAE-dextran procedure and cultured according to the previously reported method (Kojima, N. et al., FEBS Lett., 360, pp.1–4, 1995). After 48 hr transfection, the culture medium was collected and the protein A-mouse STX expressed in the medium was adsorbed to IgG-Sepharose (15 μl of resin per 10 ml of culture medium) at 4° C. for 16 hr. The resin was collected by centrifugation, washed three times with phosphate-buffered saline, suspended in 50 μl (final volume) of Dulbecco's modified Eagle medium without fetal bovine serum, and used as the soluble enzyme.

The enzyme assays of the fused protein of the present invention and product characterizations were performed as follows: the enzyme activity was measured according to the method reported by Sasaki et al. (Sasaki, K. et al., J. Biol. Chem. 269, pp.15950–15956, 1994) in the presence of 0.1 M sodium cacodylate buffer (pH 6.0), 10 mM $MgCl_2$, 2 mM $CaCl_2$, 0.5% Triton CF-54, 100 μCMP-[$^{14}$C]NeuAc (0.25 μCi), 10 μg acceptor substrate, and 2 μl enzyme preparation in a total volume of 10 μl. After 4 hr incubation at 37° C., the reaction was terminated by the addition of SDS-PAGE loading buffer (10 μl), and the incubation mixtures were directly subjected to SDS-PAGE for glycoprotein acceptors.

For glycolipid acceptors, the incubation mixtures were applied on a C-18 column (Sep-Pak Vac, 100 mg; Waters, Milford, Mass., U.S.A.) which was washed with water. The glycolipids were eluted from the column with methanol, dried, and then subjected to chromatography on an HPTLC plate (Merck, Germany) with a solvent system of chloroform, methanol, and 0.02% $CaCl_2$ (55:45:10) according to the aforementioned method (Sasaki, K. et al., J. Biol. Chem., 269, pp.15950–15956, 1994). Acceptor substrates were visualized by staining with Coomassie Brilliant Blue for glycoproteins or by the orcinol/$H_2SO_4$ method for glycolipids. The radioactive materials in glycoproteins or glycolipids were visualized with a BAS2000 radio image analyzer (Fuji Film, Japan), and the radioactivity incorporated into acceptor glycoproteins was counted.

For linkage analysis of sialic acids, fetuin sialylated with the enzyme was precipitated with 70% ethanol, washed three times with 70% ethanol, dissolved in water, and then digested with a linkage-specific recombinant sialidase, NANase I (specific for α 2,3-linked sialic acids, 0.1 U/ml), NANase II (specific for α 2,3-and α 2,6-linked sialic acids, 0.5 U/ml), or NANase III (specific for α 2,3-, α 2,6-, and α 2,8-linked sialic acids, 0.35 U/ml)(FACE, Glyko, Inc., Navato, Calif.) at 37° C. for 8 hr.

For preparation of de-sialylated or de-N-glycosylated fetuin, fetuin (100 μg) was digested with NANase I (0.1 U/ml), NANase II (0.5 U/ml), or NANase III (0.35 U/ml) in a total volume of 20 μl for 24 hr at 37° C., or with N-glycanase (1.5 U; Genzyme, Cambridge, Mass.) in a total volume of 20 μl at 37° C. for 36 hr. After inactivation of the enzyme by boiling for 1 min, the resulting de-sialylated or de-N-glycosylated glycoproteins were used as acceptors.

Various glycoproteins were incubated with the fused protein of the present invention (i.e. Siaα 2,3Galβ 1,4GlcNAcα 2,8-sialyltransferase in the form of the protein A-fused soluble enzyme), and then the reaction mixtures were analyzed by SDS-PAGE. When fetuin was used as an acceptor, strong sialyltransferase activity was detected, as seen in the case of mouse ST8Sia II. No activity toward fetuin was observed in the culture medium from cells transfected with the vector alone. Sialylated glycoproteins such as α 1-acid glycoprotein, ovomucoid, and transferrin served as acceptors. However, the fused protein did not exhibit activity toward asialoglycoproteins at all.

In addition, various glycolipids were incubated with the fused protein of the present invention, and the resulting glycolipids were analyzed by HPTLC with a solvent system of $CHCl_3/CH_3OH/0.2\%$ $CaCl_2$ (55:45:10). $^{14}$C-Sialic acid incorporation from CMP-[$^{14}$C]NeuAc was also observed when GM3 was used as an acceptor substrate, as seen in the case of GD3 synthase ST8Sia I). The fused protein of the present invention exhibits low activity toward GD3. 2,3-SPG (Siaα 2,3Galβ 1,4GlcNAc β 1,4Galβ 1,4Glcβ1,1Cer) served as the best acceptor substrate among the tested glycolipids for the fused protein of the present invention.

On the other hand, 2,6-SPG did not serve as an acceptor at all for the fused protein of the present invention. Other gangliosides, such as GM1, GD1a, GD1b, GT1b, and GQ1b, as well as neutral glycosphingolipids did not serve as acceptor substrates for the fused protein of the present invention. There was no sialyltransferase activity toward gangliosides, including 2,3-SPG, as well as neutral glycosphingolipids in the medium obtained from COS-7 cells transfected with the vector without the insert.

The product synthesized from GM3 by the fused protein of the present invention was comigrated with authentic GD3 on HPTLC with two different solvent systems. In addition, a $^{14}$C-sialylated ganglioside was eluted from DEAE- Sephadex at the position of di-sialylated gangliosides. The linkages of the incorporated sialic acids were also confirmed by digestion of $^{14}$C-sialylated fetuin with linkage-specific sialidases.

Fetuin was $^{14}$-C-sialylated with the fused protein of the present invention, and then the $^{14}$C-sialylated glycoprotein (1,000 cpm) was digested with α 2,3-specific sialidase (NANase I), α 2,3- and α 2,6-specific sialidase (NANase II), or α 2,3-, α 2,6-, and α 2,8-specific sialidase (NANase III). $^{14}$C-sialylated fetuin was also digested with N-glycanase (1.5 U) at 37° C. for 36 hr. The resulting glycoproteins were subjected to SDS-PAGE, visualized with BAS2000 image analyzer, and the residual radioactivity at the position of enzyme-treated fetuin was quantified.

The incorporated $^{14}$C-sialic acids were completely resistant to treatment with α 2,3-specific sialidase or α 2,3- and α 2,6-specific sialidase, but almost completely disappeared on treatment with α 2,3-, α 2,6-, and α 2,8-specific sialidase. The results are shown in FIG. 3. In the figure, C, I, II, III, and N represent treatment with no enzyme, NANase I, NANase II, NANase III, and N-glycanase, respectively. It is apparent from these results that the sialic acids incorporated by the fused protein of the present invention were linked to terminal sialic acids through α 2,8-linkages and Siaα 2,8Sia sequences were synthesized by the fused protein of the present invention, and thus the cloned gene λ CRO3 encoded a novel α 2,8-sialyltransferase O3 (ST8Sia III).

In view of the fact that the fused protein of the present invention exhibits activities toward 2,3-SPG and GM3 but not toward 2,6-SPG, the activity of the sialyltransferase O3 of the present invention may be specific to the Siaα 2,3Gal-sequence. This possibility was confirmed by measuring the activity toward de-sialylated fetuin. Fetuin was digested with NANase I, II, or III, and each of the resulting de-sialylated glycoproteins was incubated with the fused protein of the present invention and subjected to SDS-PAGE, and then the radioactivity incorporated into the de-sialylated glycoproteins was visualized and quantified with BAS2000 radio image analyzer.

Figure 4:
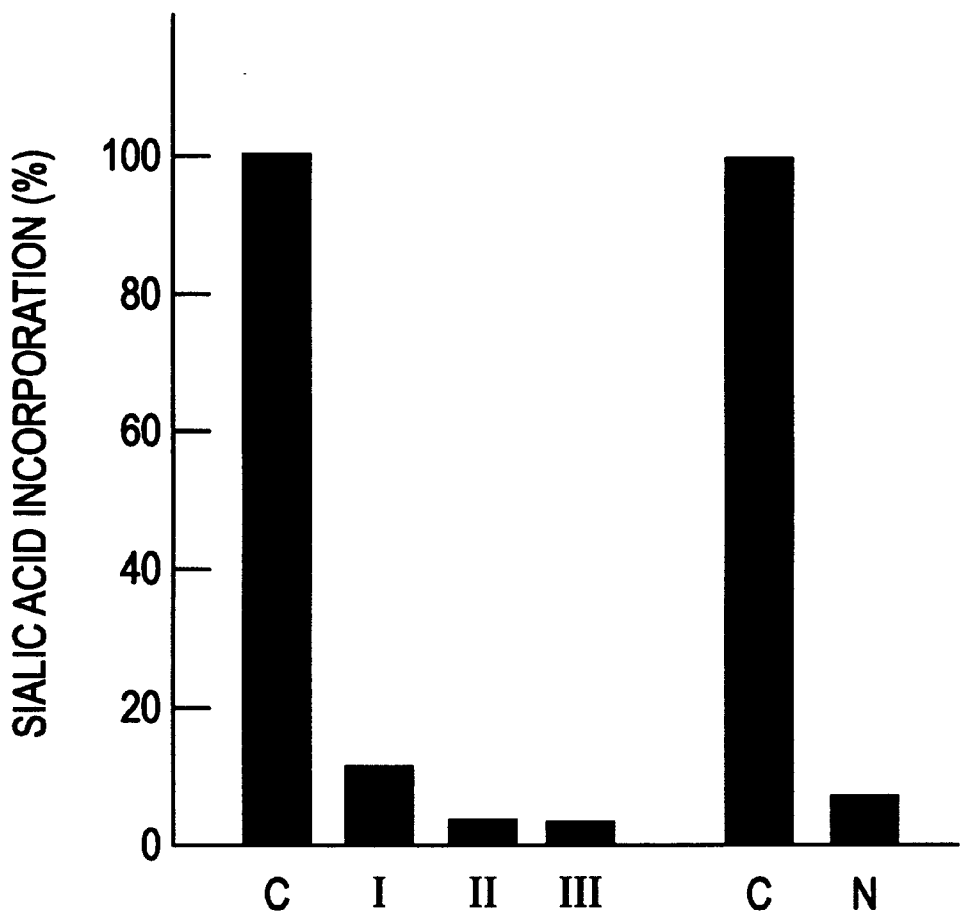
FIG. 4 shows the effects of treatment with sialidase and N-glycanase of fetuin on the activity of the α 2,8-sialyltransferase of the present invention. In the figure, C, I, II, III, and N represent treatment with no enzyme, NANase I, NANase II, and NANase III, and N-glycanase, respectively.

The results are shown in FIG. 4. In the figure, C, I, II, and III represent treatment with no enzyme, NANase I, NANase II, and NANase III, respectively. Glycoproteins were first digested with N-glycanase. The resulting de-N-glycosylated glycoproteins were then incubated with the fused protein of the present invention and CMP-[$^{14}$C]NeuAc, and the incorporated sialic acids were visualized and counted. Symbols C and N represent treatments with no enzyme and N-glycanase, respectively.

The activity of the fused protein of the present invention toward de-sialylated fetuin on treatment with α 2,3-specific sialidase, as well as that on treatment with α 2,3- and α 2,6-specific sialidase or α 2,3-, α 2,6-, and α 2,8-specific sialidase, was completely abolished. Under the same digestion conditions, α 2,3-SPG was desialylated by α 2,3-specific sialidase, but 2,6-SPG was completely resistant toward treatment with α 2,3-specific sialidase.

To determine whether the sialic acids are incorporated into N-linked oligosaccharides or O-linked oligosaccharides of fetuin, $^{14}$C-sialylated fetuin was digested with N-glycanase. The sialic acids incorporated into fetuin were completely released from the proteins, and N-glycanase-treated fetuin did not serve as an acceptor (FIG. 4). Since GD1a, GT1b, GQ1b, and O-linked oligosaccharides in fetuin, which contain Siaα 2,3Galβ 1,3GalNAc sequences, did not serve as acceptors for the fused protein of the present invention, and 2,3-SPG was a good acceptor for it, the activities of the fused protein are specific for the Siaα 2,3Galβ 1,4GalNAc sequences of N-linked oligosaccharides of glycoproteins as well as glycolipids.

TABLE 1

Comparison of the Acceptor Substrate Specificities of Three Cloned α 2,8-Sialyltransferases.

| Acceptors | ST8Sia III | ST8Sia II (STX) | ST8Sia I[1] (GD3 synthase) |
|---|---|---|---|
| | (pmol/ml medium, h) | | |
| (Glycoproteins) | | | |
| α 1-Acid glycoprotein | 7.8 | 7.6 | 0[2] |
| Asialo-α 1-acid glycoprotein | 0 | 0 | 0 |
| Fetuin | 92.1 | 8.0 | 0 |
| Asialofetuin | 0 | 0 | 0 |
| Ovomucoid | 1.7 | 1.3 | 0 |
| Transferrin (Bovine) | 1.3 | 0.38 | 0 |
| BSM | 0 | 0 | 0 |
| (Glycolipids) | | | |
| Lactosylceramide | 0 | 0 | 0 |
| GM3 | 2.1 | 0 | 0.18 |
| GD3 | 0.86 | 0 | 0 |
| GM1 | 0 | 0 | 0 |
| GD1a | 0 | 0 | 0 |
| GD1b | 0 | 0 | 0 |
| GT1b | 0 | 0 | 0 |
| GQ1b | 0 | 0 | 0 |
| 2,3-SPG | 7.5 | 0 | N.T.[3] |
| 2,6-SPG | 0 | 0 | N.T. |

[1] Human ST8SiaI (GD3 synthase) expressed by Namalwa cells was used (Sasaki, K. et al., J. Biol. Chem. 269, pp.15950–15956, 1994).
[2] 0 indicates values under 0.1 pmol/ml medium, h for mouse ST8Sia II and III, and those under 0.01 pmol/ml medium, h for human ST8Sia I.
[3] N.T. indicates not tested.

The acceptor substrate specificity of the sialyltransferase of the present invention was compared to those of so far cloned α 2,8-sialyltransferases, GD3 synthase (ST8Sia I) and STX (ST8Sia II), as shown in Table 1. STX exhibited sialyltranfer activity only toward sialylated glycoproteins such as α 1-acid glycoproteins or fetuin, i.e. no activity being detected toward glycolipids including GM3 and 2,3-SPG, while GD3 synthase exhibited activity only toward GM3, but not toward sialylated glycoproteins. Comparison of the substrate specificities of these two α 2,8-sialyltransferases revealed that the sialyltransferase of the present invention has rather broader activity.

Both sialylated glycoproteins and glycolipids served as acceptors for the sialyltransferase of the present invention. Although the substrate specificities for glycoproteins of the sialyltransferase of the present invention and ST8Sia II were similar to each other, fetuin acts as a better acceptor (10 fold) than α1-acid glycoprotein for the sialyltransferase of the present invention. For ST8Sia II, the incorporation of sialic acids into fetuin was almost the same as the sialic acid incorporation into α-acid glycoprotein. Thus, the structure of oligosaccharides on glycoproteins acting as acceptors for the sialyltransferase of the present invention is different from that in the case of ST8Sia II.

The substrate specificity of the sialyltransferase of the present invention toward glycolipids was rather similar to the substrate specificity of ST8Sia I (GD3 synthase), i.e. both sialyltransferases synthesized GD3 from GM3. However, the sialyltransferase of the present invention is characterized by the activity of synthesizing GT3 from GD3, which is not achieved by ST8Sia I. In addition, the sialyltransferase of the present invention has activity of introducing several units of sialic acid into the substrates.

The apparent Km values of the sialyltransferase of the present invention for 2,3-SPG GM3, and GD3 were 68 μM, 588 μM, and 3,300 μM, respectively (Table 2). The Vmax/Km values set out in Table 2 clearly show that 2,3-SPG is a much more suitable acceptor for the sialyltransferase of the present invention as compared to GM3 or GD3. In addition, the Vmax/Km values for fetuin indicate that the sialyltransferase of the present invention has remarkably higher specificity toward complex-type N-linked oligosaccharides containing Siaα 2,3Galβ 1,4GlcNAc sequence.

TABLE 2

Kinetic properties of the sialyltransferase of the present invention

| Acceptors | Km (mM) | Vmax (pmol/h,ml) | Vmax/Km |
|---|---|---|---|
| 2,3-SPG | 0.082 | 9.2 | 112.1 |
| GM3 | 0.588 | 3.7 | 6.3 |
| GD3 | 3.30 | 6.1 | 1.8 |
| Fetuin[1)] | 0.020 | 424 | 21200 |

[1)]The numbers of α 2,3-linked sialic cids on N-linked oligosaccharides (about 30 nmol/mg) were calculated from the difference between sialic acid residues in fetuin and those in α 2,3-specific sialidase-treated fetuin, and the number of O-linked oligosaccharides (about 70 nmol/mg).

To evaluate the expression pattern and message size of the cloned gene that encodes the sialyltransferase of the present invention, total RNAs were isolated from several mouse tissues: brain, heart, liver, lung, kidney, spleen, salivary gland, thymus, testis, and placenta. Each of RNAs (5 μg) prepared from various adult mouse tissues was subjected to Nothern blot hybridization analysis using the 1205-bp XhoI fragment of the cloned cDNA of the sialyltransferase of the present invention as hybridization probe.

5 μg of tatal RNA was fractionated on a denaturing formaldehyde-agarose gel (1%) and then transferred onto a nylon membrane (Nytran, Schleicher & Schuell). The full-length of ST8Sia-III cDNA (1205-bp) was amplified b: PCR using synthetic oligonucleotide primers (5'-AGG CTCGAGCTCTCAATGGACCGATT-3' and 5'-TTCCAT CTCGAGTTCTTAGGCACAGTGTGACAG-3') from 3-day-old mouse brain cDNA. The full length mouse GD3 synthase and mouse STX fragments (Kojima, N. et al., FEBS Lett., 360, pp.1–4, 1995) were prepared by PCR amplification, subcloned and sequenced. These fragments were radiolabeled and used as probes.

Three RNA species of 6.7-, 2.2-, and 1.7-kb were expressed in brain. Strong expression of a 3.7-kb transcript was observed in testis, but not in brain. The distribution of these transcripts was similar to that in the case of STX (ST8Sia II). The inventors of the present invention reported that the expression of the STX (ST8Sia II) gene was detected in fetal and newborn mouse brain (Kojima, N. et al., FEBS Lett., 360, pp.1–4, 1995). In order to compare ST8Sia III gene with other α 2,8-sialyltransferase genes as to transcription patterns during mouse brain development, total RNAs (5 μg each) prepared from the brains of 14 and 20 p.c. fetal, and 3-day-, 2-week-, and 8-week-old mice was analyzed by Northern blot hybridization. As probes, full length cDNAs for the sialyltransferase of the present invention, mouse ST8Sia II (STX), and mouse STSia I (GD3 synthase) were used.

The transcripts of the sialyltransferase of the present invention first appeared in 20 p.c. fetal brain and then decreased in successive development. On the other hand, a 6.0-kb transcript of ST8Sia II was detected in 14 p.c. fetal brain and then the level of the transcript increased up to the peak level of 20 p.c. fetal brain. After then, ST8Sia II message decreased to an almost undetectable level within 2 weeks after the birth. An approximately 9-kb transcript of ST8Sia I was also expressed in the brain throughout development, its level being highest in 20 p.c. fetal brain. These results suggest that each of the three enzyme genes is expressed differently during brain development.

It has been shown that poly-α 2,8-sialosyl sialyltransferase activity is restricted to an early stege of development (McCoy, R. D. et al., J. Biol. Chem., 260, pp.12695–12699, 1985). A Golgi-enriched fraction from 20-day-old fetal rat brain contains poly α 2,8-sialosyl sialyltransferase activity toward N-CAM in vitro. However, a membrane fraction isolated from adult rat brain contains lower sialyltransferase activity and no poly-α 2,8-sialosyl sialyltransferase activity. From the results of chemical analysis (Finne, J., J. Biol. Chem., 257, pp.11966–11970, 1982) and overexpression of Galβ 1,4GlcNAcα 2,6-sialyltransferase during Xenopus embryogenesis (Livingston, B. D. et al., Glycobiology 1, pp.39–44, 1990), it was suggested that the polysialic acids are attached to Siaα 2,3-Gal-residues of an N-linked oligosaccharides. The gene expression pattern and substrate specificity of the sialyltransferase of the present invention suggested that the present sialyltransferase is very closely involved in the initial step of sialic acid polymerization, i.e. biosynthesis of Siaα 2,8Siaα 2,3Gal of N-glycan.

ST8sia II (STX), which was highly regulated furing development of the brain, also exhibits α 2,8-sialyltransferase activity and polysialic acid synthase activity solely toward N-linked oligosaccharides of glycoproteins, and thus it was suggested that the enzyme is involved in polvsialic acid chain biosynthesis (Kojima, N. et al., FEBS Lett., 360, pp.1–4, 1995, and FEBS Lett., 373, pp.119–122, 1995). The structures of N-linked oligosaccharides as acceptors for ST8Sia II (STX) and the sialyltransferase of the present invention are essentially distinct in vivo, even if they overlap in part, for the following reasons: 1) the sialyltransferase of the present invention but not ST8Sia II exhibited activity toward 2,3-SPG; 2) incorporation of sialic acids into fetuin was 10-fold greater than that into α1-acid glycoproteins in the case of the sialyltransferase of the present invention, whereas that into fetuin and α1-acid glycoproteins was almost the same in that of ST8Sia II.

Since 2,3- and 2,6-SPGs did not serve as acceptors for mouse ST8Sia II, ST8Sia II may require not only the NeuAc α 2,3Galβ 1,4GlcNAc sequence but also a more complex structure containing the NeuAcα 2,3Galβ 1,4GlcNAc sequence for α2,8-sialyltransfer. On the other hand, the minimum structural requirement for sialyltransfer by the sialyltransferase of the present invention is Siaα 2,3Galβ 1,4GlcNAc-R.

The reason why two different types of α2,8-sialyltransferase with similar substrate specificities toward N-linked oligosaccharide exist in mouse brain is not clear at present. One possibility is that the glycoproteins which act as acceptor substrates for ST8Sia II (STX) and the sialyltransferase of the present invention are different. Indeed, at least two brain glycoproteins, i.e. N-CAM and the α subunit of voltage-gated sodium channels, are known to be polysialylated (Edelman, G. M., Annu. Rev. Biochem. 54, pp.135–169, 1985; Cunningham, B. A. et al., Science, 236, pp.799–806, 1987; Rutishauser, U. et al., Science, 240, pp.53–57, 1983; Zuber, C., J. Biol. Chem., 267, pp.9965–9971, 1992). Thus, ST8Sia II and the sialyltransferase of the present invention are possibly involved in the biosynthesis of polysialic acid of N-CAM and the α subunit of voltage-gated sodium channels, respectively.

Another possibility is that the two enzymes have almost the same substrate specificity in vivo, but are con-rolled through different regulation systems. The gene expression of ST8Sia II (STX) and that of the sialyltransferase of the present invention during brain development are distinguishable from each other. ST8Sia II appeared first in 14 p.c. fetal brain and then completely disappeared, at least in 2-week-old mouse brain. In contrast, the gene of the sialyltransferase of the present invention was not expressed in 14 p.c. fetal brain. However, its expression was observed in 20 p.c. fetal brain, and although the expression was decreased during development, the enzyme was still expressed in 2-week old mouse brain.

It has been reported that the expression of polysialic acids of N-CAM is developmentally regulated, i.e. the embryonic form with a high sialic acid content undergoes postnatal conversion to the adult form with a low sialic acid content, although the core structure of N-linked oligosaccharides attached to polysialic acid chains during brain development have not been fully studied (Zuber, C., J. Biol. Chem. 267, pp.9965–9971, 1992; Hoffman, S. et al., J. Biol. Chem. 257, pp.7720–7729, 1982; Edelman, G. M., Science, 219, 450–457, 1983). ST8Sia II and the sialyltransferase of the present invention may be responsible for the polysialic acid chain biosynthesis of the embryonic and postnatal forms of N-CAM, respectively.

In the experiments set out above, unless otherwise specifically mentioned, the materials used were essentially the same as those described in the following publications: Sasaki, K. et al., J. Biol. Chem. 269, pp.15950–15956, 1994; Kurosawa, N. et al., J. Biol. Chem., 269, pp.1402–1409, 1994; Lee, Y.-C. et al., J. Biol. Chem., 269, pp.10028–10033, 1994; and Kurosawa, N. et al., J. Biol. Chem., 269, pp.19048–19053, 1994.

Lactosylceramide, GM3, GD3, GD1a, GD1b, and GT1b were purchased from Sigma (St. Louis, Mo., USA); and GQ1b and paragloboside were from IATRON (Tokyo, Japan). α 2,3- and α 2,6-sialylparaglobosides (SPGs) were gifts from Dr. Iwamori, Tokyo University. Glycoproteins (fetuin, asialofetuin, a 1 acid glycoprotein, ovomucoid, transferrin, and bovine submaxillary mucin) were from Sigma. Asialo- α1-acid glycoprotein and asialo-ovomucoid were prepared by mild acid hydrolysis of glycoproteins (0.02N, HCl, 80° C., 1 h), Protein A-sepharose was from Pharmacia.

We claim:

1. An isolated and purified DNA encoding Siaα2,3Galβ1, 4GlcNAc α2,8-sialyltransferase having the amino acid sequence:

```
Met Leu Ser Val Ala Leu Leu Ile Leu Ser Leu       15
                            Ile Ser Tyr Val

Ser Leu Lys Lys Glu Asn Ile Phe Thr Thr Pro       30
                            Lys Tyr Ala Ser

Pro Gly Ala Pro Arg Met Tyr Met Phe His Ala       45
                            Gly Phe Arg Ser

Gln Phe Ala Leu Lys Phe Leu Asp Gln Ser Phe       60
                            Val Pro Ile Thr

Asn Ser Leu Thr His Glu Leu Gln Glu Lys Pro       75
                            Ser Lys Trp Thr

Phe Asn Arg Thr Ala Phe Leu His Gln Arg Gln       90
                            Glu Ile Leu Gln

His Val Asp Val Ile Lys Asn Phe Ser Leu Thr      105
                            Lys Ser Ser Val

Arg Ile Gly Gln Leu Met His Tyr Asp Tyr Ser      120
                            Ser His Lys Tyr

Val Phe Ser Ile Ser Asn Asn Phe Arg Ser Leu      135
                            Leu Pro Asp Val

Ser Pro Ile Met Asn Lys Arg Tyr Asn Val Cys      150
                            Ala Val Val Gly

Asn Ser Gly Ile Leu Thr Gly Ser Gln Cys Gly      165
                            Gln Glu Ile Asp

Lys Ser Asp Phe Val Ser Arg Cys Asn Phe Ala      180
                            Pro Thr Glu Ala

Phe His Lys Asp Val Gly Arg Lys Thr Asn Leu      195
                            Thr Thr Phe Asn

Pro Ser Ile Leu Glu Lys Tyr Tyr Asn Asn Leu      210
                            Leu Thr Ile Gln

Asp Arg Asn Asn Phe Phe Leu Ser Leu Lys Lys      225
                            Leu Asp Gly Ala

Ile Leu Trp Ile Pro Ala Phe Phe Phe His Thr      240
                            Ser Ala Thr Val

Thr Arg Thr Leu Val Asp Phe Phe Val Glu His      255
                            Arg Gly Gln Leu

Lys Val Gln Leu Ala Trp Pro Gly Asn Ile Met      270
                            Gln His Val Asn

Arg Tyr Trp Lys Asn Lys His Leu Ser Pro Lys      285
                            Arg Leu Ser Thr

Gly Ile Leu Met Tyr Thr Leu Ala Ser Ala Ile      300
                            Cys Glu Glu Ile

His Leu Tyr Gly Phe Trp Pro Phe Gly Phe Asp      315
                            Pro Asn Thr Arg

Glu Asp Leu Pro Tyr His Tyr Tyr Asp Lys Lys      330
                            Gly Thr Lys Phe

Thr Thr Lys Trp Gln Glu Ser His Gln Leu Pro      345
                            Ala Glu Phe Gln

Leu Leu Tyr Arg Met His Gly Glu Gly Leu Thr      360
                            Lys Leu Thr Leu

Ser His Cys Ala(364)(SEQ. ID. NO:1).
```

2. The DNA according to claim 1 having the nucleic acid sequence:

```
ATG CTC AGC GTG GCC CTG CTG ATT TTA TCG CTT ATC AGC TAC GTG    45  (SEQ.ID.NO:2).
TCT CTG AAA AAG GAG AAC ATC TTC ACC ACT CCC AAG TAC GCC AGC    90
CCG GGG GCG CCC CGA ATG TAC ATG TTC CAC GCG GGA TTC CGG TCA   135
CAG TTT GCA CTG AAG TTT CTA GAC CAG TCA TTT GTG CCC ATT ACG   180
AAT TCT CTC ACC CAT GAA CTC CAA GAG AAA CCT TCT AAA TGG ACA   225
TTT AAT CGG ACA GCG TTT TTA CAT CAA AGG CAA GAA ATT CTT CAG   270
CAT GTC GAT GTA ATA AAA AAT TTT TCT TTG ACC AAG AGT AGT GTT   315
CGG ATT GGA CAA CTA ATG CAT TAT GAT TAT TCC AGC CAT AAA TAT   360
GTC TTC TCG ATT AGC AAT AAC TTC CGG TCC CTG CTC CCA GAT GTG   405
TCG CCC ATT ATG AAT AAG CGT TAT AAT GTT TGT GCT GTG GTT GGA   450
AAC AGT GGA ATC TTG ACA GGG AGT CAG TGT GGA CAA GAA ATA GAT   495
AAA TCA GAT TTT GTT TCT CGA TGC AAT TTT GCC CCG ACA GAG GCT   540
TTC CAC AAA GAT GTT GGA AGG AAA ACC AAC CTC ACA ACC TTC AAT   585
CCG AGC ATC TTA GAG AAA TAT TAC AAC AAT CTT TTA ACC ATT CAG   630
GAC CGT AAC AAC TTC TTC CTC AGT TTA AAA AAG CTT GAT GGG GCC   675
ATA CTT TGG ATC CCT GCA TTT TTC TTC CAC ACT TCT GCA ACT GTA   720
ACG AGA ACG CTA GTG GAT TTT TTT GTT GAG CAC AGA GGT CAG TTA   765
AAG GTC CAG TTG GCT TGG CCT GGA AAT ATC ATG CAA CAT GTC AAC   810
AGG TAC TGG AAA AAC AAA CAC CTG TCA CCC AAA CGA CTG AGC ACA   855
GGT ATC CTA ATG TAT ACT CTT GCA TCT GCA ATA TGT GAA GAG ATC   900
CAC TTG TAC GGT TTC TGG CCC TTT GGA TTT GAC CCC AAC ACC AGG   945
GAG GAT CTG CCC TAC CAC TAC TAT GAC AAA AAA GGA ACC AAA TTT   990
ACC ACC AAG TGG CAG GAG TCT CAC CAG CTG CCT GCT GAG TTT CAG  1035
CTG CTC TAT CGA ATG CAT GGG GAA GGG CTC ACG AAG CTC ACT CTG  1080
TCA CAC TGT GCC TAA(1095)
```

3. An isolated DNA encoding an the enzymatically active domain of the Siaα2,3Galβ1,4GlcNAc α2,8-sialyltransferase according to claim 1, which domain is capable of catalyzing Siaα2,3Galβ1,4GlcNAc α2,8-sialyltransfer.

4. An isolated DNA encoding a polypeptide comprising an enzymatically active domain of the Siaα2,3Galβ1,4GlcNAc α2,8-sialyltransferase according to claim 1, which domain is capable of catalyzing Siaα2,3Galβ1,4GlcNAc α2,8-sialyltransfer, operably linked to DNA encoding at least one signal peptide.

5. An isolated DNA encoding an extracellularly releasable protein comprising an enzymatically active domain of the Siaα2,3Galβ1,4GlcNAc α2,8-sialyltransferase according to claim 1, which domain is capable of catalyzing Siaα2,3Galβ1,4GlcNAc α2,8-sialyltransfer, operably linked to DNA encoding at least one signal peptide.

6. The DNA according to claim 5 having the sequence:

```
CCC AAG TAC GCC AGC CCG GGG GCG CCC CGA ATG TAC ATG TTC CAC    45  (SEQ.ID.NO.4).
GCG GGA TTC CGG TCA CAG TTT GCA CTG AAG TTT CTA GAC CAG TCA    90
TTT GTG CCC ATT ACG AAT TCT CTC ACC CAT GAA CTC CAA GAG AAA   135
CCT TCT AAA TGG ACA TTT AAT CGG ACA GCG TTT TTA CAT CAA AGG   180
CAA GAA ATT CTT CAG CAT GTC GAT GTA ATA AAA AAT TTT TCT TTG   225
ACC AAG AGT AGT GTT CGG ATT GGA CAA CTA ATG CAT TAT GAT TAT   270
TCC AGC CAT AAA TAT GTC TTC TCG ATT AGC AAT AAC TTC CGG TCC   315
CTG CTC CCA GAT GTG TCG CCC ATT ATG AAT AAG CGT TAT AAT GTT   360
TGT GCT GTG GTT GGA AAC AGT GGA ATC TTG ACA GGG AGT CAG TGT   405
```

```
GGA CAA GAA ATA GAT AAA TCA GAT TTT GTT TCT CGA TGC AAT TTT 450

GCC CCG ACA GAG GCT TTC CAC AAA GAT GTT GGA AGG AAA ACC AAC 495

CTC ACA ACC TTC AAT CCG AGC ATC TTA GAG AAA TAT TAC AAC AAT 540

CTT TTA ACC ATT CAG GAC CGT AAC AAC TTC TTC CTC AGT TTA AAA 585

AAG CTT GAT GGG GCC ATA CTT TGG ATC CCT GCA TTT TTC TTC CAC 630

ACT TCT GCA ACT GTA ACG AGA ACG CTA GTG GAT TTT TTT GTT GAG 675

CAC AGA GGT CAG TTA AAG GTC CAG TTG GCT TGG CCT GGA AAT ATC 720

ATG CAA CAT GTC AAC AGG TAC TGG AAA AAC AAA CAC CTG TCA CCC 765

AAA CGA CTG AGC ACA GGT ATC CTA ATG TAT ACT CTT GCA TCT GCA 810

ATA TGT GAA GAG ATC CAC TTG TAC GGT TTC TGG CCC TTT GGA TTT 855

GAC CCC AAC ACC AGG GAG GAT CTG CCC TAC CAC TAC TAT GAC AAA 900

AAA GGA ACC AAA TTT ACC ACC AAG TGG CAG GAG TCT CAC CAG CTG 945

CCT GCT GAG TTT CAG CTG CTC TAT CGA ATG CAT GGG GAA GGG CTC 990

ACG AAG CTC ACT CTG TCA CAC TGT GCC TAA(1020)
```

7. A recombinant vector comprising the DNA according to claim 1.

8. A microorganism transformed by the recombinant vector according to claim 7.

9. A recombinant vector comprising the DNA according to claim 5.

10. A microorganism transformed by the recombinant vector according to claim 9.

11. A process for preparing an extracellularly releasable protein comprising the enzymatically active domain of Siaα2,3Galβ1,4GlcNAc α2,8-sialyltransferase, capable of catalyzing Siaα2,3Galβ1,4GlcNAc α2,8-sialyltransfer, operable linked to at least one signal peptide, which process comprises culturing a microorganism hosting a recombinant vector comprising the DNA according to claim 5 and recovering the protein.

* * * * *

UNITED STATES PATENT AND TRADEMARK OFFICE
CERTIFICATE OF CORRECTION

PATENT NO. : 6,017,743
DATED : January 25, 2000
INVENTOR(S) : S. TSUJI et al.

It is certified that error appears in the above-identified patent and that said Letters Patent is hereby corrected as shown below:

At column 23, line 53 (claim 1, line 16) of the printed patent, "ASp" should be ---Asp---.

At column 28, line 28 (claim 11, line 5) of the printed patent, "operable" should be ---operably---.

Signed and Sealed this

Third Day of April, 2001

Attest:

NICHOLAS P. GODICI

Attesting Officer  Acting Director of the United States Patent and Trademark Office

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
(A) LENGTH: 364 amino acids
(B) TYPE: amino acid
(C) STRANDEDNESS: Not Relevant
(D) TOPOLOGY: linear (xi) SEQUENCE DESCRIPTION: SEQ ID NO:1:

```
Met Leu Ser Val Ala Leu Leu Ile Leu Ser Leu Ile Ser Tyr Val
1               5                   10                  15

Ser Leu Lys Lys Glu Asn Ile Phe Thr Thr Pro Lys Tyr Ala Ser
                20                  25                  30

Pro Gly Ala Pro Arg Met Tyr Met Phe His Ala Gly Phe Arg Ser
                35                  40                  45

Gln Phe Ala Leu Lys Phe Leu Asp Gln Ser Phe Val Pro Ile Thr
                50                  55                  60

Asn Ser Leu Thr His Glu Leu Gln Glu Lys Pro Ser Lys Trp Thr
                65                  70                  75

Phe Asn Arg Thr Ala Phe Leu His Gln Arg Gln Glu Ile Leu Gln
                80                  85                  90

His Val Asp Val Ile Lys Asn Phe Ser Leu Thr Lys Ser Ser Val
                95                  100                 105

Arg Ile Gly Gln Leu Met His Tyr Asp Tyr Ser Ser His Lys Tyr
                110                 115                 120

Val Phe Ser Ile Ser Asn Asn Phe Arg Ser Leu Leu Pro Asp Val
                125                 130                 135

Ser Pro Ile Met Asn Lys Arg Tyr Asn Val Cys Ala Val Val Gly
                140                 145                 150

Asn Ser Gly Ile Leu Thr Gly Ser Gln Cys Gly Gln Glu Ile Asp
                155                 160                 165

Lys Ser Asp Phe Val Ser Arg Cys Asn Phe Ala Pro Thr Glu Ala
                170                 175                 180

Phe His Lys Asp Val Gly Arg Lys Thr Asn Leu Thr Thr Phe Asn
                185                 190                 195
```

```
Pro Ser Ile Leu Glu Lys Tyr Tyr Asn Asn Leu Leu Thr Ile Gln
            200                 205                 210

Asp Arg Asn Asn Phe Phe Leu Ser Leu Lys Lys Leu Asp Gly Ala
            215                 220                 225

Ile Leu Trp Ile Pro Ala Phe Phe His Thr Ser Ala Thr Val
            230                 235                 240

Thr Arg Thr Leu Val Asp Phe Phe Val Glu His Arg Gly Gln Leu
            245                 250                 255

Lys Val Gln Leu Ala Trp Pro Gly Asn Ile Met Gln His Val Asn
            260                 265                 270

Arg Tyr Trp Lys Asn Lys His Leu Ser Pro Lys Arg Leu Ser Thr
            275                 280                 285

Gly Ile Leu Met Tyr Thr Leu Ala Ser Ala Ile Cys Glu Glu Ile
            290                 295                 300

His Leu Tyr Gly Phe Trp Pro Phe Gly Phe Asp Pro Asn Thr Arg
            305                 310                 315

Glu Asp Leu Pro Tyr His Tyr Tyr Asp Lys Lys Gly Thr Lys Phe
            320                 325                 330

Thr Thr Lys Trp Gln Glu Ser His Gln Leu Pro Ala Glu Phe Gln
            335                 340                 345

Leu Leu Tyr Arg Met His Gly Glu Gly Leu Thr Lys Leu Thr Leu
            350                 355                 360

Ser His Cys Ala
        364

(2) INFORMATION FOR SEQ ID NO:2:

(i) SEQUENCE CHARACTERISTICS:
        (A) LENGTH: 1660 bases
        (B) TYPE: nucleic acid
        (C) STRANDEDNESS: Not Relevant
        (D) TOPOLOGY: linear (xi) SEQUENCE DESCRIPTION: SEQ ID NO:2:

GG CACGAGGCCA GCAGGCTGCT                          22

GGCGCTCAAT GGACCGATTT CCCCGGTTTC CCTGAACCCA GCCTAGCCCG               72

GGATGAGAAA TTGCAAAATG GCCCGAGTCG CCAGTGTGCT AGGGCTGGTC              122

ATG CTC AGC GTG GCC CTG CTG ATT TTA TCG CTT ATC AGC TAC GTG         167
Met Leu Ser Val Ala Leu Leu Ile Leu Ser Leu Ile Ser Tyr Val
1               5                   10                  15

TCT CTG AAA AAG GAG AAC ATC TTC ACC ACT CCC AAG TAC GCC AGC         212
Ser Leu Lys Lys Glu Asn Ile Phe Thr Thr Pro Lys Tyr Ala Ser
                20                  25                  30

CCG GGG GCG CCC CGA ATG TAC ATG TTC CAC GCG GGA TTC CGG TCA         257
Pro Gly Ala Pro Arg Met Tyr Met Phe His Ala Gly Phe Arg Ser
                35                  40                  45

CAG TTT GCA CTG AAG TTT CTA GAC CAG TCA TTT GTG CCC ATT ACG         302
Gln Phe Ala Leu Lys Phe Leu Asp Gln Ser Phe Val Pro Ile Thr
                50                  55                  60

AAT TCT CTC ACC CAT GAA CTC CAA GAG AAA CCT TCT AAA TGG ACA         347
Asn Ser Leu Thr His Glu Leu Gln Glu Lys Pro Ser Lys Trp Thr
                65                  70                  75

TTT AAT CGG ACA GCG TTT TTA CAT CAA AGG CAA GAA ATT CTT CAG         392
Phe Asn Arg Thr Ala Phe Leu His Gln Arg Gln Glu Ile Leu Gln
                80                  85                  90

CAT GTC GAT GTA ATA AAA AAT TTT TCT TTG ACC AAG AGT AGT GTT         437
His Val Asp Val Ile Lys Asn Phe Ser Leu Thr Lys Ser Ser Val
                95                  100                 105
```

-continued

| | |
|---|---|
| CGG ATT GGA CAA CTA ATG CAT TAT GAT TAT TCC AGC CAT AAA TAT<br>Arg Ile Gly Gln Leu Met His Tyr Asp Tyr Ser Ser His Lys Tyr<br>110                        115                    120 | 482 |
| GTC TTC TCG ATT AGC AAT AAC TTC CGG TCC CTG CTC CCA GAT GTG<br>Val Phe Ser Ile Ser Asn Asn Phe Arg Ser Leu Leu Pro Asp Val<br>125                        130                    135 | 527 |
| TCG CCC ATT ATG AAT AAG CGT TAT AAT GTT TGT GCT GTG GTT GGA<br>Ser Pro Ile Met Asn Lys Arg Tyr Asn Val Cys Ala Val Val Gly<br>140                        145                    150 | 572 |
| AAC AGT GGA ATC TTG ACA GGG AGT CAG TGT GGA CAA GAA ATA GAT<br>Asn Ser Gly Ile Leu Thr Gly Ser Gln Cys Gly Gln Glu Ile Asp<br>155                        160                    165 | 617 |
| AAA TCA GAT TTT GTT TCT CGA TGC AAT TTT GCC CCG ACA GAG GCT<br>Lys Ser Asp Phe Val Ser Arg Cys Asn Phe Ala Pro Thr Glu Ala<br>170                        175                    180 | 662 |
| TTC CAC AAA GAT GTT GGA AGG AAA ACC AAC CTC ACA ACC TTC AAT<br>Phe His Lys Asp Val Gly Arg Lys Thr Asn Leu Thr Thr Phe Asn<br>185                        190                    195 | 707 |
| CCG AGC ATC TTA GAG AAA TAT TAC AAC AAT CTT TTA ACC ATT CAG<br>Pro Ser Ile Leu Glu Lys Tyr Tyr Asn Asn Leu Leu Thr Ile Gln<br>200                        205                    210 | 752 |
| GAC CGT AAC AAC TTC TTC CTC AGT TTA AAA AAG CTT GAT GGG GCC<br>Asp Arg Asn Asn Phe Phe Leu Ser Leu Lys Lys Leu Asp Gly Ala<br>215                        220                    225 | 797 |
| ATA CTT TGG ATC CCT GCA TTT TTC TTC CAC ACT TCT GCA ACT GTA<br>Ile Leu Trp Ile Pro Ala Phe Phe Phe His Thr Ser Ala Thr Val<br>230                        235                    240 | 842 |
| ACG AGA ACG CTA GTG GAT TTT TTT GTT GAG CAC AGA GGT CAG TTA<br>Thr Arg Thr Leu Val Asp Phe Phe Val Glu His Arg Gly Gln Leu<br>245                        250                    255 | 887 |
| AAG GTC CAG TTG GCT TGG CCT GGA AAT ATC ATG CAA CAT GTC AAC<br>Lys Val Gln Leu Ala Trp Pro Gly Asn Ile Met Gln His Val Asn<br>260                        265                    270 | 932 |
| AGG TAC TGG AAA AAC AAA CAC CTG TCA CCC AAA CGA CTG AGC ACA<br>Arg Tyr Trp Lys Asn Lys His Leu Ser Pro Lys Arg Leu Ser Thr<br>275                        280                    285 | 977 |
| GGT ATC CTA ATG TAT ACT CTT GCA TCT GCA ATA TGT GAA GAG ATC<br>Gly Ile Leu Met Tyr Thr Leu Ala Ser Ala Ile Cys Glu Glu Ile<br>290                        295                    300 | 1022 |
| CAC TTG TAC GGT TTC TGG CCC TTT GGA TTT GAC CCC AAC ACC AGG<br>His Leu Tyr Gly Phe Trp Pro Phe Gly Phe Asp Pro Asn Thr Arg<br>305                        310                    315 | 1067 |
| GAG GAT CTG CCC TAC CAC TAC TAT GAC AAA AAA GGA ACC AAA TTT<br>Glu Asp Leu Pro Tyr His Tyr Tyr Asp Lys Lys Gly Thr Lys Phe<br>320                        325                    330 | 1112 |
| ACC ACC AAG TGG CAG GAG TCT CAC CAG CTG CCT GCT GAG TTT CAG<br>Thr Thr Lys Trp Gln Glu Ser His Gln Leu Pro Ala Glu Phe Gln<br>335                        340                    345 | 1157 |
| CTG CTC TAT CGA ATG CAT GGG GAA GGG CTC ACG AAG CTC ACT CTG<br>Leu Leu Tyr Arg Met His Gly Glu Gly Leu Thr Lys Leu Thr Leu<br>350                        355                    360 | 1202 |
| TCA CAC TGT GCC TAA<br>Ser His Cys Ala --- | 1217 |
| GAACTCCAAA TGGAAAGTGC AAACGGCTG ATTAAAAAGT GCCCTCACCC | 1267 |
| CCAAACCAAA TTGAATAGTC TCCAGAACAG AACCCATAGA CAATCTGGCA | 1317 |
| AAGCCTGTCT GCCACTTACA AGGAAAGACG CCTTCTCTTC CTCTTTTGCA | 1367 |
| CTGCTCTTTG AATGGTCTTA ACAAACTTAG GACAGGTGCA TTGAAGCCGT | 1417 |

-continued

```
GTGATTTAGA CTTGATTGGG AAAAGGTTAT ATTGCATTTG GAAGTATGCT         1467

GCACAGAGAA TAGCTTGAAA TAGTTCTAAG TTTGTATTTT AATAATAAAC         1517

CGACTCCCAT GTGAATGAGG AATGTGACTG TCATCTCCTC CTCTCTACTT         1567

TGATATAGTC CTCACAACCA GGGAGCTCTG GCCAGCTCCA GCAGGATCTC         1617

TTTAGCCAAG GGGATCAGAA TCTTCAAAAA AAAAAAAAAA AAA               1660
```

(2) INFORMATION FOR SEQ ID NO:3:

(i) SEQUENCE CHARACTERISTICS:
        (A) LENGTH: 339 amino acids
        (B) TYPE: amino acid
        (C) STRANDEDNESS: Not Relevant
        (D) TOPOLOGY: linear (xi) SEQUENCE DESCRIPTION: SEQ ID NO:3:

```
Pro Lys Tyr Ala Ser Pro Gly Ala Pro Arg Met Tyr Met Phe His
 1               5                  10                  15

Ala Gly Phe Arg Ser Gln Phe Ala Leu Lys Phe Leu Asp Gln Ser
                20                  25                  30

Phe Val Pro Ile Thr Asn Ser Leu Thr His Glu Leu Gln Glu Lys
                35                  40                  45

Pro Ser Lys Trp Thr Phe Asn Arg Thr Ala Phe Leu His Gln Arg
                50                  55                  60

Gln Glu Ile Leu Gln His Val Asp Val Ile Lys Asn Phe Ser Leu
                65                  70                  75

Thr Lys Ser Ser Val Arg Ile Gly Gln Leu Met His Tyr Asp Tyr
                80                  85                  90

Ser Ser His Lys Tyr Val Phe Ser Ile Ser Asn Asn Phe Arg Ser
                95                 100                 105

Leu Leu Pro Asp Val Ser Pro Ile Met Asn Lys Arg Tyr Asn Val
               110                 115                 120

Cys Ala Val Val Gly Asn Ser Gly Ile Leu Thr Gly Ser Gln Cys
               125                 130                 135

Gly Gln Glu Ile Asp Lys Ser Asp Phe Val Ser Arg Cys Asn Phe
               140                 145                 150

Ala Pro Thr Glu Ala Phe His Lys Asp Val Gly Arg Lys Thr Asn
               155                 160                 165

Leu Thr Thr Phe Asn Pro Ser Ile Leu Glu Lys Tyr Tyr Asn Asn
               170                 175                 180

Leu Leu Thr Ile Gln Asp Arg Asn Asn Phe Phe Leu Ser Leu Lys
               185                 190                 195

Lys Leu Asp Gly Ala Ile Leu Trp Ile Pro Ala Phe Phe Phe His
               200                 205                 210

Thr Ser Ala Thr Val Thr Arg Thr Leu Val Asp Phe Phe Val Glu
               215                 220                 225

His Arg Gly Gln Leu Lys Val Gln Leu Ala Trp Pro Gly Asn Ile
               230                 235                 240

Met Gln His Val Asn Arg Tyr Trp Lys Asn Lys His Leu Ser Pro
               245                 250                 255

Lys Arg Leu Ser Thr Gly Ile Leu Met Tyr Thr Leu Ala Ser Ala
               260                 265                 270

Ile Cys Glu Glu Ile His Leu Tyr Gly Phe Trp Pro Phe Gly Phe
               275                 280                 285

Asp Pro Asn Thr Arg Glu Asp Leu Pro Tyr His Tyr Tyr Asp Lys
               290                 295                 300
```

```
Lys Gly Thr Lys Phe Thr Thr Lys Trp Gln Glu Ser His Gln Leu
            305                 310                 315

Pro Ala Glu Phe Gln Leu Leu Tyr Arg Met His Gly Glu Gly Leu
            320                 325                 330

Thr Lys Leu Thr Leu Ser His Cys Ala
            335             339
```

(2) INFORMATION FOR SEQ ID NO:4:

(i) SEQUENCE CHARACTERISTICS:
        (A) LENGTH: 1048 bases
        (B) TYPE: nucleic acid
        (C) STRANDEDNESS: Not Relevant
        (D) TOPOLOGY: linear (xi) SEQUENCE DESCRIPTION: SEQ ID NO:4:

```
                                          CAT CTTCTCGAGT           13

CCC AAG TAC GCC AGC CCG GGG GCG CCC CGA ATG TAC ATG TTC CAC        58
Pro Lys Tyr Ala Ser Pro Gly Ala Pro Arg Met Tyr Met Phe His
1               5                   10                  15

GCG GGA TTC CGG TCA CAG TTT GCA CTG AAG TTT CTA GAC CAG TCA        103
Ala Gly Phe Arg Ser Gln Phe Ala Leu Lys Phe Leu Asp Gln Ser
                20                  25                  30

TTT GTG CCC ATT ACG AAT TCT CTC ACC CAT GAA CTC CAA GAG AAA        148
Phe Val Pro Ile Thr Asn Ser Leu Thr His Glu Leu Gln Glu Lys
                35                  40                  45

CCT TCT AAA TGG ACA TTT AAT CGG ACA GCG TTT TTA CAT CAA AGG        193
Pro Ser Lys Trp Thr Phe Asn Arg Thr Ala Phe Leu His Gln Arg
                50                  55                  60

CAA GAA ATT CTT CAG CAT GTC GAT GTA ATA AAA AAT TTT TCT TTG        238
Gln Glu Ile Leu Gln His Val Asp Val Ile Lys Asn Phe Ser Leu
                65                  70                  75

ACC AAG AGT AGT GTT CGG ATT GGA CAA CTA ATG CAT TAT GAT TAT        283
Thr Lys Ser Ser Val Arg Ile Gly Gln Leu Met His Tyr Asp Tyr
                80                  85                  90

TCC AGC CAT AAA TAT GTC TTC TCG ATT AGC AAT AAC TTC CGG TCC        328
Ser Ser His Lys Tyr Val Phe Ser Ile Ser Asn Asn Phe Arg Ser
                95                  100                 105

CTG CTC CCA GAT GTG TCG CCC ATT ATG AAT AAG CGT TAT AAT GTT        373
Leu Leu Pro Asp Val Ser Pro Ile Met Asn Lys Arg Tyr Asn Val
                110                 115                 120

TGT GCT GTG GTT GGA AAC AGT GGA ATC TTG ACA GGG AGT CAG TGT        418
Cys Ala Val Val Gly Asn Ser Gly Ile Leu Thr Gly Ser Gln Cys
                125                 130                 135

GGA CAA GAA ATA GAT AAA TCA GAT TTT GTT TCT CGA TGC AAT TTT        463
Gly Gln Glu Ile Asp Lys Ser Asp Phe Val Ser Arg Cys Asn Phe
                140                 145                 150

GCC CCG ACA GAG GCT TTC CAC AAA GAT GTT GGA AGG AAA ACC AAC        508
Ala Pro Thr Glu Ala Phe His Lys Asp Val Gly Arg Lys Thr Asn
                155                 160                 165

CTC ACA ACC TTC AAT CCG AGC ATC TTA GAG AAA TAT TAC AAC AAT        553
Leu Thr Thr Phe Asn Pro Ser Ile Leu Glu Lys Tyr Tyr Asn Asn
                170                 175                 180

CTT TTA ACC ATT CAG GAC CGT AAC AAC TTC TTC CTC AGT TTA AAA        598
Leu Leu Thr Ile Gln Asp Arg Asn Asn Phe Phe Leu Ser Leu Lys
                185                 190                 195

AAG CTT GAT GGG GCC ATA CTT TGG ATC CCT GCA TTT TTC TTC CAC        643
Lys Leu Asp Gly Ala Ile Leu Trp Ile Pro Ala Phe Phe Phe His
                200                 205                 210

ACT TCT GCA ACT GTA ACG AGA ACG CTA GTG GAT TTT TTT GTT GAG        688
```

-continued

```
Thr Ser Ala Thr Val Thr Arg Thr Leu Val Asp Phe Phe Val Glu
                215                 220                 225

CAC AGA GGT CAG TTA AAG GTC CAG TTG GCT TGG CCT GGA AAT ATC       733
His Arg Gly Gln Leu Lys Val Gln Leu Ala Trp Pro Gly Asn Ile
                230                 235                 240

ATG CAA CAT GTC AAC AGG TAC TGG AAA AAC AAA CAC CTG TCA CCC       778
Met Gln His Val Asn Arg Tyr Trp Lys Asn Lys His Leu Ser Pro
                245                 250                 255

AAA CGA CTG AGC ACA GGT ATC CTA ATG TAT ACT CTT GCA TCT GCA       823
Lys Arg Leu Ser Thr Gly Ile Leu Met Tyr Thr Leu Ala Ser Ala
                260                 265                 270

ATA TGT GAA GAG ATC CAC TTG TAC GGT TTC TGG CCC TTT GGA TTT       868
Ile Cys Glu Glu Ile His Leu Tyr Gly Phe Trp Pro Phe Gly Phe
                275                 280                 285

GAC CCC AAC ACC AGG GAG GAT CTG CCC TAC CAC TAC TAT GAC AAA       913
Asp Pro Asn Thr Arg Glu Asp Leu Pro Tyr His Tyr Tyr Asp Lys
                290                 295                 300

AAA GGA ACC AAA TTT ACC ACC AAG TGG CAG GAG TCT CAC CAG CTG       958
Lys Gly Thr Lys Phe Thr Thr Lys Trp Gln Glu Ser His Gln Leu
                305                 310                 315

CCT GCT GAG TTT CAG CTG CTC TAT CGA ATG CAT GGG GAA GGG CTC      1003
Pro Ala Glu Phe Gln Leu Leu Tyr Arg Met His Gly Glu Gly Leu
                320                 325                 330

ACG AAG CTC ACT CTG TCA CAC TGT GCC TAA                          1033
Thr Lys Leu Thr Leu Ser His Cys Ala ---
                335                 339

GAACTCGAGA TGGAA                                                 1048
```